United States Patent [19]
Landis et al.

[11] Patent Number: 5,676,677
[45] Date of Patent: Oct. 14, 1997

[54] GUARD FOR THE BLADE OF A KNIFE

[76] Inventors: Robert M. Landis, 1130 Puddingstone Rd., Mountainside, N.J. 07092; Mark A. Adelman, 75 Clinton Ave., Millburn, N.J. 07041

[21] Appl. No.: 619,215

[22] Filed: Mar. 21, 1996

[51] Int. Cl.$^6$ .................................................. A61B 17/32
[52] U.S. Cl. ............................................. 606/167; 30/162
[58] Field of Search .............................. 606/167, 170, 606/172, 181; 30/162, 335, 339, 155, 286

[56] References Cited

U.S. PATENT DOCUMENTS

| | | | |
|---|---|---|---|
| 2,650,424 | 9/1953 | Kalmon | 30/286 |
| 4,089,112 | 5/1978 | Richards | 30/162 |
| 5,250,064 | 10/1993 | Schneider | 606/167 |
| 5,258,001 | 11/1993 | Corman | 606/167 |
| 5,330,492 | 7/1994 | Haugen | 606/167 |
| 5,344,424 | 9/1994 | Roberts et al. | 606/167 |
| 5,417,704 | 5/1995 | Wonderley | 606/167 |
| 5,431,672 | 7/1995 | Cote et al. | 606/167 |
| 5,478,346 | 12/1995 | Capewell | 606/167 |
| 5,496,340 | 3/1996 | Abidin et al. | 606/167 |
| 5,522,828 | 6/1996 | Malilay | 606/167 |

*Primary Examiner*—Michael Buiz
*Assistant Examiner*—Tina T. D. Pham
*Attorney, Agent, or Firm*—Morgan & Finnegan, L.L.P.

[57] ABSTRACT

A shield is provided for a surgical scalpel having a handle and a blade secured thereto. In one embodiment, the shield is slidably engaged with the blade, and movable between a position covering the cutting edge of the blade and a position exposing the cutting edge of the blade. An actuation mechanism is coupled to the shield for moving the shield between the position covering the cutting edge and the position exposing the cutting edge. In another embodiment, the shield is pivotally and frictionally engaged to the blade while still allowing the shield to be moved between a position covering the cutting edge of the blade and a position exposing the cutting edge of the blade. An actuation mechanism is included to cause the travel of the shield between the two positions.

14 Claims, 4 Drawing Sheets

GUARD FOR THE BLADE OF A KNIFE

FIELD OF THE INVENTION

The present invention relates generally to surgical knife assemblies including blades with cutting edges and in particular to a guard for the blade of a surgical scalpel.

BACKGROUND OF THE INVENTION

Scalpels and similar types of cutting instruments which include sharp cutting edges are routinely used by surgeons, physicians and other medical personnel in surgical procedures and the like. Typically, the scalpels used have an exposed sharp cutting edge. In the busy environment of an operating room where surgical instruments are passed between physician and assistants quickly and frequently, the exposed cutting edge of a scalpel creates a real hazard of accidental cutting. More importantly, the cutting edge may be contaminated with various infectious viruses which can be transmitted through cuts when even small quantities of blood come into contact.

Recently, with the advent of various infectious diseases, such as AIDS, the virus of which may be transferred to individuals through operating room cuts, there has been an increased awareness of preventing such accidents. The idea has developed from protecting the patient to protecting both the patient and the caregiver. Now there is routine use of masks, gloves, and fluidproof garments while performing any procedures involving body fluids in the hospital, whereas in years past, these "infection control" items were only used in sterile procedures. While these items are routinely used, there are two areas that remain dangerous for the Operating Room staff. As can be understood, the unprotected scalpel blade has become an area of great concern to physicians, nurses, hospital administrators, and the health care industry as a whole.

Scalpels and other knife edges having a removable guard to cover sharp cutting edges have been known in the art. For example, U.S. Pat. No. 3,945,117 to Beaver describes a surgical blade with an adjustable blade guard. However, in the device disclosed by Beaver, two handed manipulation is required since the guard does not automatically return to cover the cutting edge of the blade. As can be understood, the hazard of accidental injury remains. U.S. Pat. Nos. 5,071,426 and 5,139,507 to Dolgin et al. disclose a surgical scalpel with a retractable blade guard that incorporates an expensive and complex actuating mechanism in the handle of the scalpel to provide movement of the blade guard. Unfortunately, a surgeon utilizing this device sacrifices the "feel" of the scalpel handle to use the guard.

Thus, there is a need for a blade guard that would facilitate the safe passage of a scalpel from one person to another which may be adapted to currently available scalpel handles so that a surgeon's familiar tactile sense will not be impeded during use.

Accordingly, it is an object of the present invention to provide a guard for the cutting edge of a scalpel blade that can be moved without requiring a two-handed operation.

It is another object of the present invention to provide a guard for the cutting edge of a scalpel blade that can be adapted to currently available scalpel handles while not impeding a surgeon's tactile sense or visual field during use.

It is a further object of the present invention to provide a guard for the cutting edge of a scalpel blade that is simple in design and use, and economical to manufacture.

The foregoing objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

In accordance with these and other objects of the present invention, a brief summary of an exemplary embodiment is presented. Some simplifications and omissions may be made in the following summary, which is intended to highlight and introduce some aspects of the present invention, but not to limit its scope. Detailed descriptions of exemplary embodiments adequate to allow those of ordinary skill in the art to make and use the inventive concepts will be provided later.

The invention in its broader aspects contemplates a scalpel having an elongated handle having a proximal end and distal end; a blade secured to the distal end of the handle, the blade having a cutting edge along its side edge thereof; a shield slidably engaged with the blade, and movable between a position covering the cutting edge of the blade and a position exposing the cutting edge of the blade; and an actuation mechanism coupled to the shield for moving the shield between the position covering the cutting edge and the position exposing the cutting edge. In another embodiment, the shield is pivotally and frictionally engaged to the blade while still allowing the shield to be moved between a position covering the cutting edge of the blade and a position exposing the cutting edge of the blade. Additionally, the shield is lockable so that the blade is effectively disabled. Alternatively, the shield might be anchored to the blade itself.

The principal advantage of a handle mounted guard would be that it would adapt to the currently available handles and the currently available blades. The disadvantages arise from the fact that the guard mount materially alters the handle. It changes the "feel" of the handle. Additionally, it appreciably increases the size of device as the guard would have two components—the guard itself, and the mounting component that holds it to the handle.

The principal advantage of the blade mount lies in that it in no way alters the scalpel handle. The device is smaller as the mounting component would be the blade itself. With a smaller device and transparent guard, there would be minimal impairment to the surgeons' visual field, tactile sense, and access to the surgical field. The primary disadvantage would lie in the fact that the blade would be altered to accommodate the mounting of the guard necessitating the retooling of blade production.

DETAILED DESCRIPTION OF PREFERRED EMBODIMENTS OF THE PRESENT INVENTION

Figure 1B:
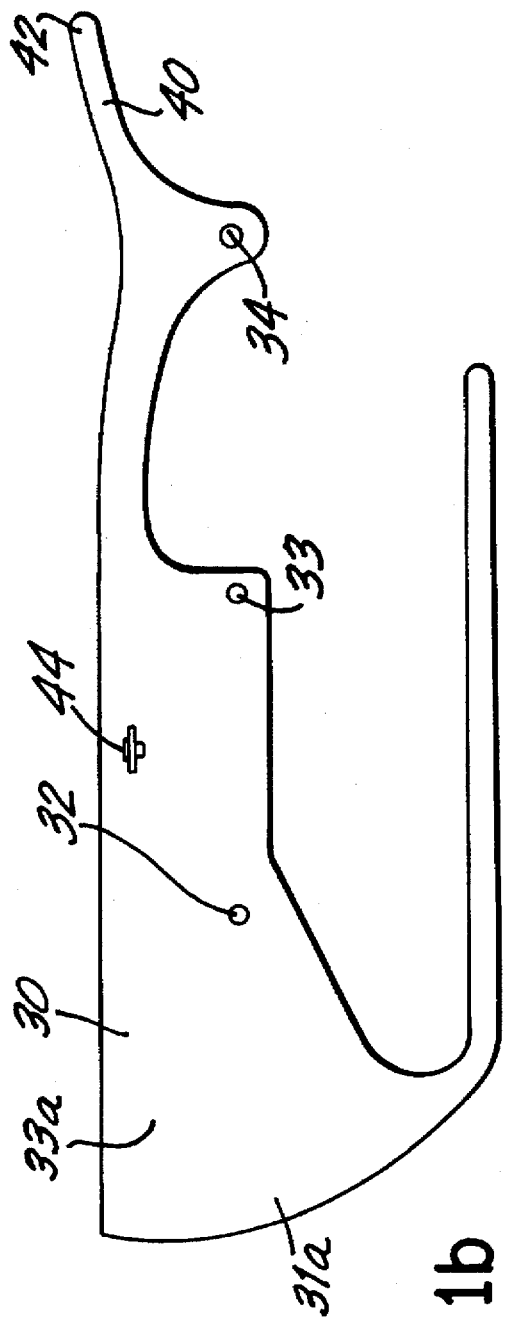
FIG. 1b is a side sectional view of an embodiment of a guard within the scope of the present invention.
Figure 1A:
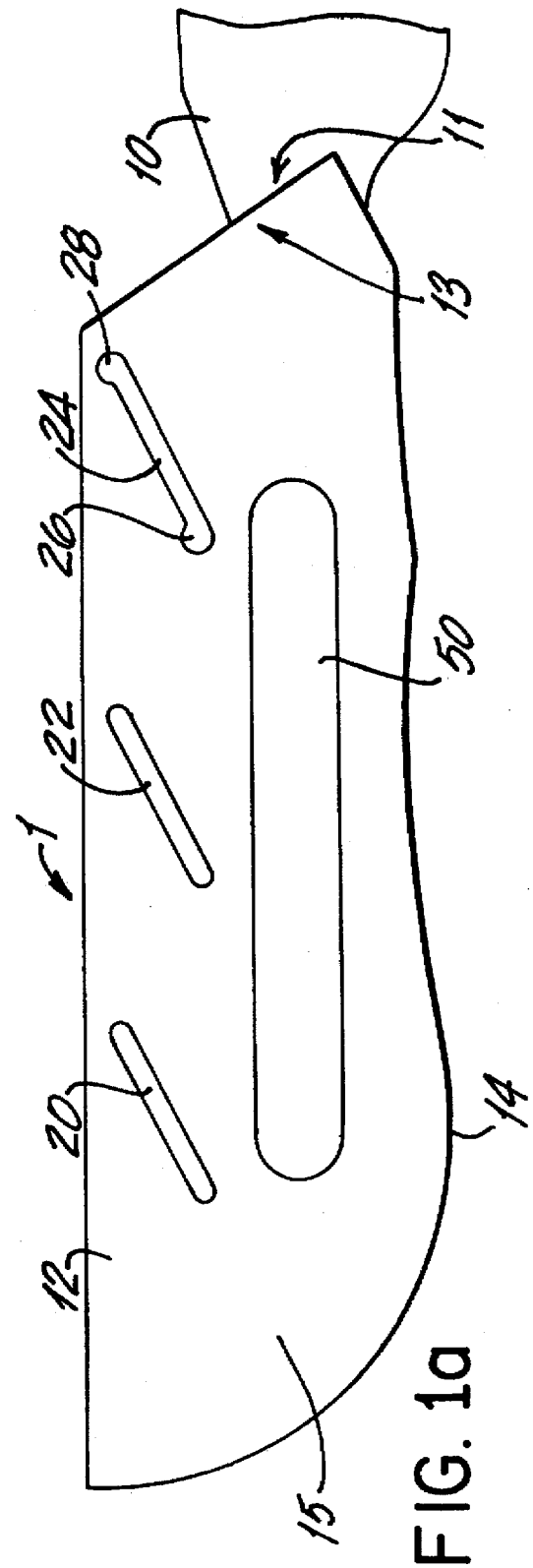
FIG. 1a is a side sectional view of a first preferred embodiment of a scalpel blade of the present invention.

The present invention contemplates a shield for the blade of a surgical knife assembly such as a scalpel, to protect persons handling the scalpel from accidentally receiving cuts and exposing themselves to the transmission of possibly infectious diseases.

Referring now to the drawings, wherein like numerals refer to like objects, there is disclosed in FIGS. 1–6 broad aspects of the invention. FIGS. 1(a) and 1(b) illustrate a first preferred embodiment of a surgical scalpel of the present invention.

Broadly stated, the scalpel 1 comprises an elongate handle section generally designated 10, and a flat blade 12 having a cutting edge 14. The blade 12 includes a distal cutout 20 and a proximal cutout 24 and a cutout 22 located between the distal cutout 20 and proximal cutout 24. Proximal cutout 24 further includes recessed grooves or sockets 26 and 28 on respective ends. The functions of cutouts 20, 22 and 24 will be described in detail below. A latch 44 is provided to secure the guard 30 in place over blade 12 when the scalpel is not in use. If desired, the latch can be so constructed so that, after use, the guard 30 can be replaced over the blade and the latch activated to permanently cover the blade 12, in such a manner the scalpel 1 can be safely disposed of.

A further embodiment of the invention includes a scalpel 1, which is packaged with the guard 30 in an open position, i.e., so that blade 12 is exposed. The latch 44 is so constructed that the guard 30 after use is closed and the latch 44 automatically engages to cover the blade 12 so that the scalpel cannot be used again.

The blade 12 has a proximal end 13 and a distal end 15. The handle 10, which has a proximal end (not shown) and a distal end 11, is secured to the proximal end 13 of the blade 12 at its distal end 11. In all preferred embodiments, both the handle 10 and the blade 12 are made of a high quality stainless steel. However, it will be understood by those skilled in the art that other suitable materials may be used for the handle 10 and/or the blade 12 without departing from the scope of the invention.

Figure 2:
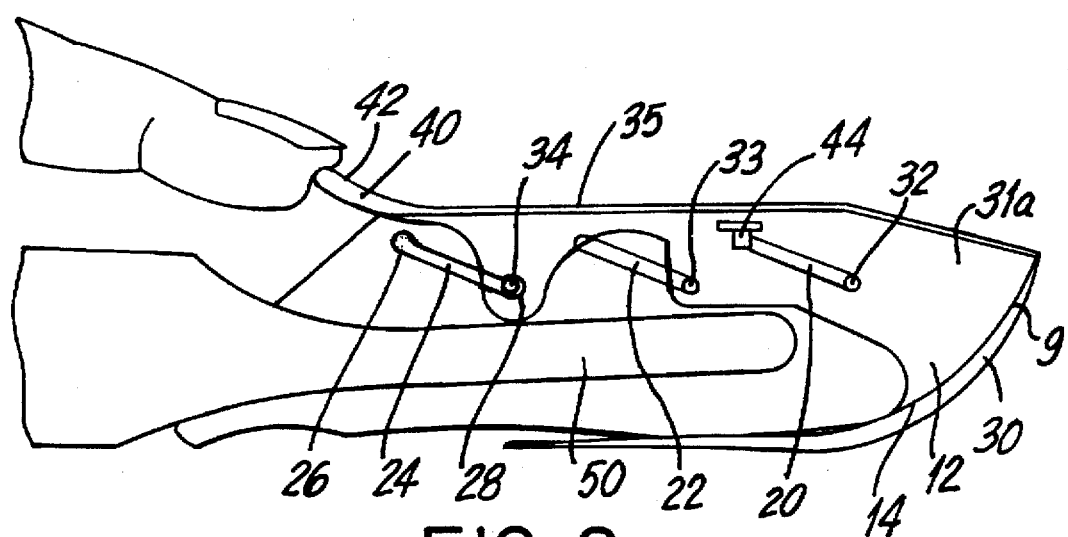
FIG. 2 is a side sectional view of a first preferred embodiment of a scalpel blade having a guard positioned to cover the cutting edge of the scalpel blade.

Turning to FIG. 2, the scalpel blade 12 is shown having a shield or guard 30 movably mounted thereon and positioned to cover the cutting edge 14. The shield 30 is mounted on the blade 12 through the use of forward pin 32 intermediate pin 33 and rear pin 34, which are disposed in cutouts 20, 22 and 24 respectively. The shield 30 extends from just beyond the distal end 15 of the blade 12, following along the cutting edge 14 in the direction of the handle 10 (not shown), so as to cover all sharp portions of the cutting edge 14.

Figure 3:
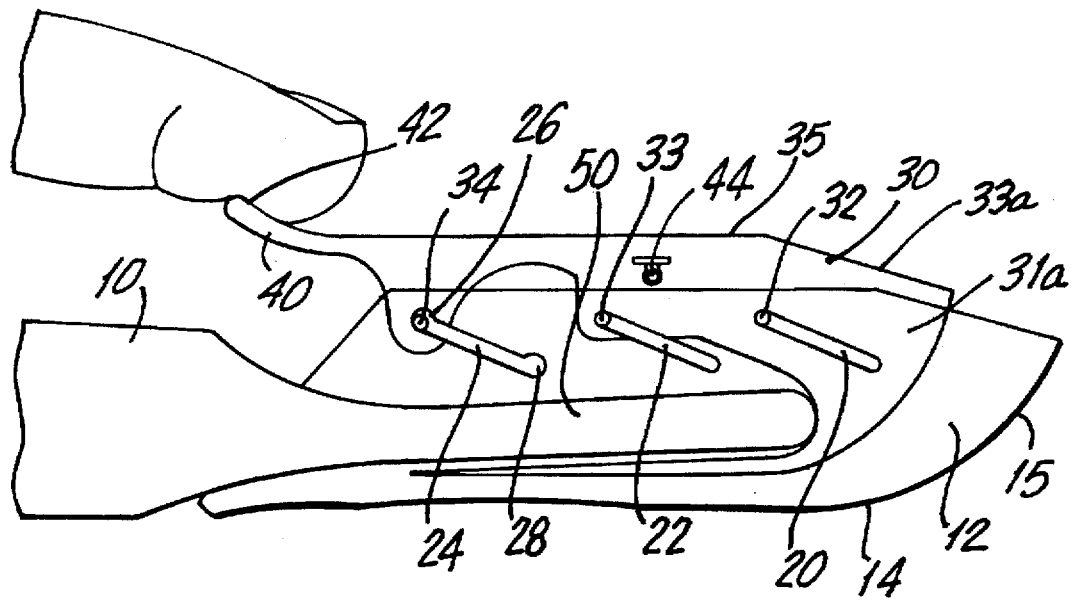
FIG. 3 is a side sectional view of a first preferred embodiment of a scalpel blade having a guard positioned to expose the cutting edge of the scalpel blade.

As illustrated in FIGS. 2 and 3, the rear or proximal portion of the shield 30 is preferably generally U-shaped so as to avoid interference with a stiffening member 50 commonly found on conventional surgical scalpels. However it should be understood that the shield 30 is not limited to the generally U-shaped illustrated in the FIGS. 1a and 1b and that a cutout suitable to avoid any interference with parts of the scalpel blade 12 may be employed in the present invention. Moreover, the shield 30 may not need to be U-shaped or contain a cutout when used with a blade that does not include any structural area which may cause interference with the positioning of the shield 30.

An actuating arm or lever 40 is coupled to the shield 30 at rear pin 34. In the first preferred embodiment, actuating arm 40 extends upward and outward from the upper proximal edge of the shield 30, projecting above the top edge of blade 12. The actuating arm 40 further includes a grip area 42 along the horizontal surface of the top of arm 40. The grip area 42 and the shape of the arm 40 are dimensioned to provide a finger rest that is comfortable during use. Advantageously, pins 32, 33 and 34 are axially disposed in their respective cutouts 20, 22 and 24 such that the pins 32, 33 and 34, are received in a low tolerance, free sliding fit that allows the pins 32, 33 and 34 to be guided in the cutouts 20, 22 and 24 when the shield 30 is moved.

The arm 40 may be secured to the shield 30 by a mechanical means, e.g. such as through the rear pin 34, or by a number of suitable means such as an adhesive, a heat/force fit, etc. Alternatively, the arm 40 may be formed integrally with the shield 30.

As shown in FIGS. 2 and 3, the shield 30 itself is bifurcated, made up of complementary planar elements 31a and 33a that are substantially parallel to each other. In the preferred embodiment, the shield elements 31a and 33a are spaced apart enough to permit blade 12 to be situated therebetween, and joined together along the upper edge portion 35. Pins 32, 33 and 34 may be used to provide a means of coupling the two shield elements 31a and 33a together while keeping them spaced apart at a set distance. Pins 32, 33 and 34 may be scored or otherwise weakened so that the shield can be easily removed if such becomes necessary. While the present scalpel is configured in such a manner that it can be used in all surgical operations, the need to remove the shield in situations where the surgical field is extremely limited.

As can be appreciated by those skilled in the art, the shield 30 need not be bifurcated into two elements 31a and 33a, and can instead comprise a single element mounted on one planar side of the blade 12 by, e.g. the pins 32, 33 and 34 that may be slidably secured in cutouts 20, 22 and 24 in suitable means known to those skilled in the art.

In FIG. 3, the shield 30 is shown in a position that permits the cutting edge 14 to be exposed. The shield 30 is positioned up and away from the distal end 15 of the blade such that pins 32, 33 and 34 are disposed at the opposite ends of the cutouts 20, 22 and 24 with respect to when the shield 30 is positioned to cover the cutting edge 14. In the exposed cutting edge 14 position, the shield 30 is moved along a path of the cutouts 20, 22 and 24 which act as guideways for the pins 32, 33 and 34.

The sockets 26 and 28 of cutout 24 provide locking positions for the shield 30 when the pin 34 is disposed therein. To facilitate the positioning of the pin 34 in the sockets 26 and 28, the portion of the shield 30 carrying pin 34 is biased upward so that it has an inherent resilience to dispose the pin 34 upward into either sprocket 26 or 28 (depending on the position of the shield 30), and consequently prevent the shield 30 from inadvertently moving with respect to the blade 12.

In all preferred embodiments, the shield 30 is made from a transparent, resilient plastic material such as polyethylene polypropylene, polyurethane, polyester, etc. so that there is a minimal impairment to the surgeon's visual field, tactile sense, and access to the surgical field.

In operation, it is anticipated that the shield 30 will normally be in the downward position covering the cutting edge 14, until the person is prepared to use the scalpel 1. A person grasping the scalpel 1 in a normal manner and wanting to move the shield 30 away from the position wherein it covers the cutting edge 14 of the blade 12 releases latch 44 and then simply applies a slight downward force to the grip area 42 of arm 40 so that pin 34 is pushed down and out of socket 26 against the inherent resilience of shield 30. Once the pin 34 is displaced out of the socket 26, a rearward force may be applied to the grip area 42 to guide the pin 34 from the socket 26 through the cutout 24 to the socket 28. Simultaneously, pins 32 and 33 are guided up along cutouts 20 and 22 towards the top ends thereof, closer to the top of blade 12. As a consequence, the shield 30 follows the same path as the pins 32, 33 and 34, causing the shield to be lifted up and away from the cutting edge 14 of the blade 12 so that the cutting edge 14 is exposed for use.

Figure 4A:
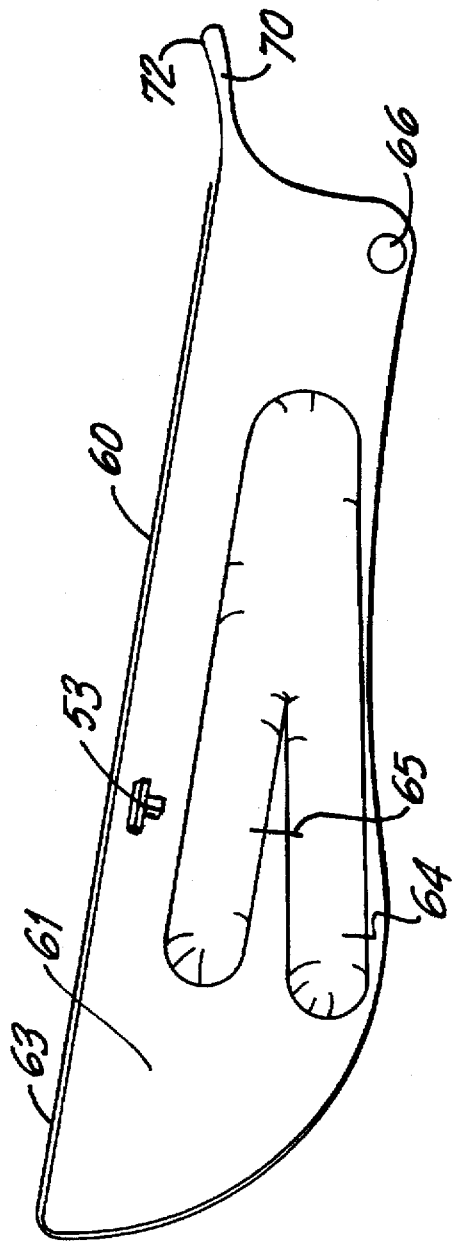
FIGS. 4(a)–(b) are prospective views of a second preferred embodiment of the present invention in which 4(a) is a side sectional view of the scalpel and 4(b) is a side sectional view of a guard which can be positioned to cover or to expose the cutting edge of the blade of the scalpel.
Figure 4B:
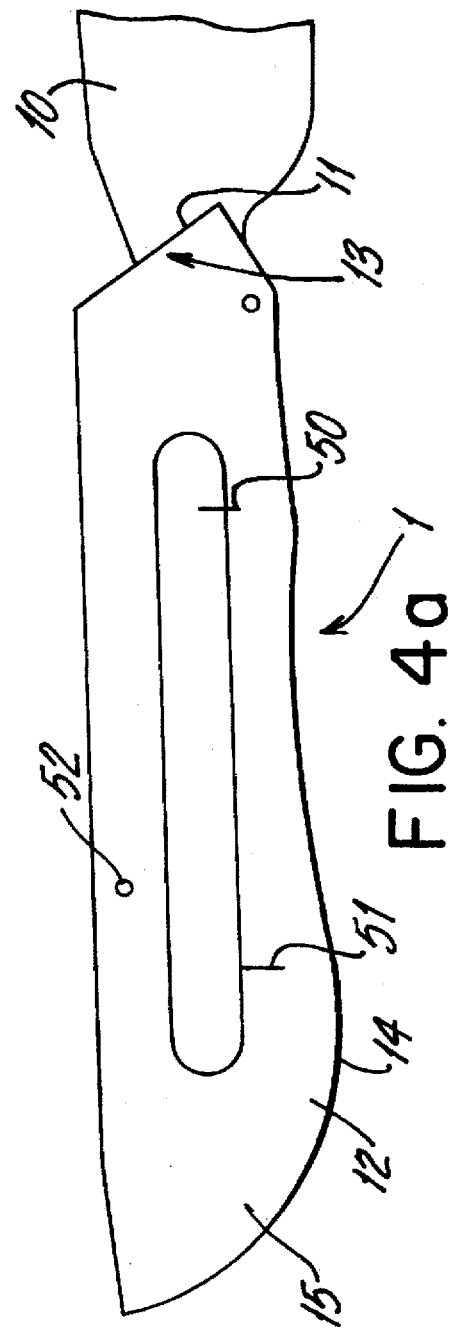

FIGS. 4(a) and 4(b) illustrate a second preferred embodiment of the scalpel 1 of the present invention. In this embodiment, elements which are essentially the same as the corresponding elements the first embodiment described above are indicated with the same reference characteristics and therefore do not require an elaborate description.

Reference will now be made to FIG. 4(a). As in the embodiment described above, the scalpel 1 generally comprises an elongate handle 10 having a distal end 11, and a blade 12 having a proximal end 13, a distal end 15, and a cutting edge 14 along one side of the blade 12. The proximal end 13 of the blade 12 is secured to the distal end 11 of the handle 10. The handle 10 has a stiffening portion 50 which is carried in a cutout portion 51 of the blade 12. Stiffening portion 50 is such that a raised portion extends in front of and behind blade 12. The blade 12 has a cutout 52 through which a latch 53 can be released to allow the guard 60 to be pivoted and, hence, to expose the blade 12 or allow the blade 12 to be covered.

The scalpel 1 further includes a bifurcated shield or guard 60 having planar elements 61 and 63 that are substantially parallel and space apart to receive the blade 12 therein. Guard 60 also has raised portions 64 and 65 which frictionally engage the sides of a stiffening member 50 located on either side of blade 12. The shield 60 is dimensioned to cover a major portion of the distal end 15 of the blade 12, including the cutting edge 14.

The two planar elements 61, 63 of the shield 60 are joined along one side, namely the side that abuts the side of the blade 12 opposite of the cutting edge 14. Extending outward from the joined ends of the planar elements 61, 63, near to the proximal end 13 of the blade 12 is a lever or arm 70 having a finger grip area 72.

Figure 6:
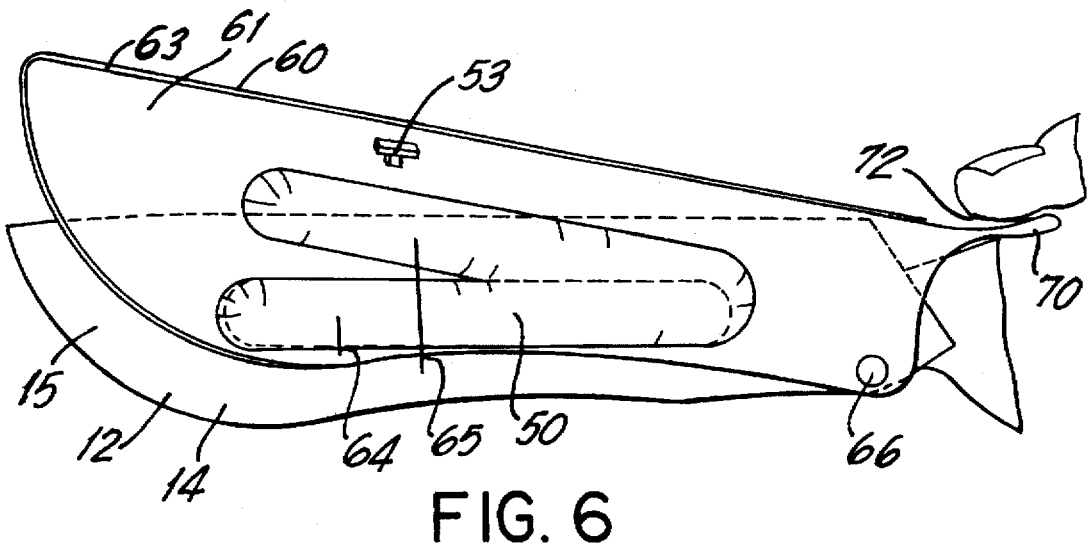
FIG. 6 is a side sectional view of a second preferred embodiment of a scalpel blade of the present invention having a guard positioned to expose the cutting edge of the blade.
Figure 5:
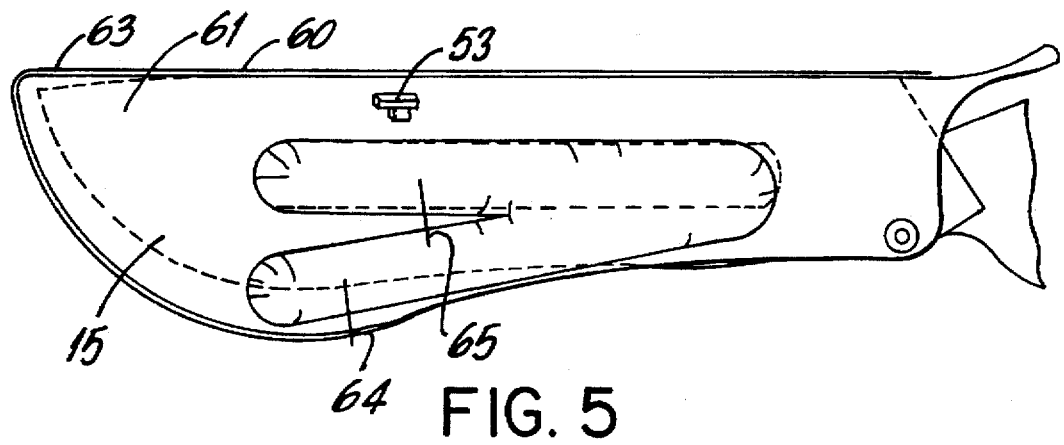
FIG. 5 is a side sectional view of a second preferred embodiment of a scalpel blade of the present invention having a guard positioned to cover the cutting edge of the scalpel blade.

As shown by the position of the shield 12 in FIGS. 5 and 6 when the arm 70 is pushed towards the blade 12, the shield 60 is caused to pivot about pivot pin 66 in pivot cutout in blade 29 about the top edge of the blade 12, causing the distal end of the shield 60 to rise and expose the cutting edge 14. Thus, in the embodiment shown, a simple and economical shield 60 can be easily moved between a position that covers and protects the cutting edge 14, and a position that allows the cutting edge 14 to be exposed prior to use.

Lastly, as in the first embodiment described above, the shield 60 in the second embodiment is preferably made from a transparent and resilient plastic that does not interfere with a surgeons visual field or tactile feel.

Moreover, although the invention has been described in detail with particular reference to several preferred embodiments thereof, it should be understood that the invention is capable of other and different embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

We claim:

1. A scalpel comprising:

an elongated handle having a proximal end and a distal end;

a blade secured to the distal end of said handle, said blade having a cutting edge along its side edge thereof;

a shield mounted on the blade and slidably engaged with said blade, and movable between a position covering said cutting edge and a position exposing said cutting edge; and an actuation means coupled to said shield for moving said shield between the position covering said cutting edge and the position exposing said cutting edge.

2. A scalpel according to claim 1, wherein said shield comprises planar elements that are positioned substantially parallel to each other and spaced apart to allow said blade to be disposed therebetween.

3. A scalpel according to claim 2 wherein said planar elements are joined together in an area located in close proximity to the opposite side of said blade from said cutting edge.

4. A scalpel according to claim 1 wherein said actuation means is a lever.

5. A scalpel according to claim 4 wherein said lever further includes a finger-grip area to facilitate manipulation of said lever by a user.

6. A scalpel according to claim 1 wherein said actuation means is integrally formed with said shield.

7. A scalpel according to claim 1 wherein said blade further includes a forward cutout, an intermediate cutout and a rear cutout, and said shield further includes a forward pin extending transversely therefrom, an intermediate pin extending transversely therefrom and a rear pin extending transversely therefrom, wherein said forward pin is disposed in said forward cutout, said intermediate pin is disposed in said intermediate cutout and said rear pin is disposed in said rear cutout so as to slidably couple said shield to said blade.

8. A scalpel according to claim 2 wherein said blade further includes a forward cutout, an intermediate cutout and a rear cutout, and said shield further includes a forward pin extending transversely therefrom an intermediate pin extending transversely therefrom and a rear pin extending transversely therefrom, wherein said forward pin is disposed in said forward cutout said intermediate pin is disposed in said intermediate cutout and said rear pin is disposed in said rear cutout so as to slidably couple said shield to said blade and secure said elements together in a spaced apart relation.

9. A scalpel according to claim 7 wherein said rear cutout further includes recessed areas on opposite ends thereof, wherein said cutout can be engaged to releasably secure said pin in said recessed areas and prevent movement of said pin and said shield relative to said blade.

10. A scalpel according to claim 8 wherein said rear cutout further includes recessed areas on opposite ends thereof, wherein said cutout can be engaged to releasably secure said pin in said recessed areas and prevent movement of said pin and said shield relative to said blade.

11. A scalpel according to claim 1, further comprising means for locking the shield so as to maintain the position covering the cutting edge or for locking the shield so as to maintain the position exposing the cutting edge.

12. A scalpel according to claim 11 wherein the means for locking can be automatically locked upon closure to ensure single use.

13. A scalpel according to claim 2, further comprising means for locking the shield so as to maintain the position covering the cutting edge or for locking the shield so as to maintain the position exposing the cutting edge.

14. A scalpel according to claim 13 wherein the means for locking can be automatically locked upon closure to ensure single use.

* * * * *